United States Patent
Joshi et al.

(10) Patent No.: US 10,777,309 B1
(45) Date of Patent: Sep. 15, 2020

(54) COMPUTING SYSTEM FOR GENERATING DELAYED ELECTRONIC PRESCRIPTIONS

(71) Applicant: Allscripts Software, LLC, Raleigh, NC (US)

(72) Inventors: Nikhil Rajeev Joshi, Pune (IN); Igor Chmil, Buffalo Grove, IL (US)

(73) Assignee: ALLSCRIPTS SOFTWARE, LLC, Raleigh, NC (US)

(*) Notice: Subject to any disclaimer, the term of this patent is extended or adjusted under 35 U.S.C. 154(b) by 249 days.

(21) Appl. No.: 15/911,039

(22) Filed: Mar. 2, 2018

(51) Int. Cl.
G16H 20/10 (2018.01)
G16H 10/60 (2018.01)
H04L 29/06 (2006.01)

(52) U.S. Cl.
CPC ............ G16H 20/10 (2018.01); G16H 10/60 (2018.01); *H04L 63/08* (2013.01); *H04L 63/123* (2013.01)

(58) Field of Classification Search
CPC ... G06F 1/00–2221/2153; G16H 10/00–80/00; G06Q 10/00–2250/905
See application file for complete search history.

(56) References Cited

U.S. PATENT DOCUMENTS

| | | | | |
|---|---|---|---|---|
| 6,988,075 B1* | 1/2006 | Hacker | ................. | G06Q 10/10 705/3 |
| 7,426,475 B1* | 9/2008 | Tangellapally | ........ | G16H 10/60 705/3 |
| 7,469,213 B1* | 12/2008 | Rao | ..................... | G06F 19/3462 705/2 |
| 7,769,601 B1* | 8/2010 | Bleser | ................... | G06F 19/326 705/3 |
| 7,890,350 B1* | 2/2011 | Fiedotin | .............. | G06F 19/3418 705/3 |
| 2003/0018495 A1* | 1/2003 | Sussman | ................ | G06Q 10/10 705/2 |
| 2003/0204415 A1* | 10/2003 | Knowlton | ............. | G06F 19/324 705/2 |
| 2005/0177392 A1* | 8/2005 | Domashnev | ........... | G06Q 50/22 705/2 |
| 2006/0259330 A1* | 11/2006 | Schranz | ................ | G06F 19/328 705/3 |
| 2009/0157424 A1* | 6/2009 | Hans | ...................... | G06Q 10/10 705/2 |

(Continued)

*Primary Examiner* — Elaine Gort
*Assistant Examiner* — Jonathon A. Szumny
(74) *Attorney, Agent, or Firm* — Medley, Behrens & Lewis, LLC (57) ABSTRACT

A computing system for generating a delayed electronic prescription for a controlled substance is disclosed herein. A server computer device receives precursor data for an electronic prescription for a controlled substance that is to be prescribed to a patient from a client computing device operated by a healthcare worker. The server computing device transmits the precursor data to a second server computing device. The second server computing device then transmits a request for an identity of a pharmacy that is to provide the controlled substance to a patient computing device operated by the patient. The patient computing device receives input causing the identity for the pharmacy to be received by the server computing device. The server computing device constructs the electronic prescription using the precursor data and the identity of the pharmacy and signs the electronic prescription with an electronic signature for the healthcare worker.

20 Claims, 7 Drawing Sheets

(56) References Cited

U.S. PATENT DOCUMENTS

| | | | | |
|---|---|---|---|---|
| 2011/0178812 A1* | 7/2011 | Lindsay | ................ | G06F 19/328 |
| | | | | 705/2 |
| 2011/0215933 A1* | 9/2011 | Darling, IV | ......... | G06Q 10/109 |
| | | | | 340/573.1 |
| 2012/0253829 A1* | 10/2012 | John | ..................... | G06Q 50/22 |
| | | | | 705/2 |
| 2013/0179180 A1* | 7/2013 | Patra | .................... | G06Q 10/00 |
| | | | | 705/2 |
| 2013/0238357 A1* | 9/2013 | Fukushi | ............. | G06F 19/3456 |
| | | | | 705/2 |
| 2013/0297333 A1* | 11/2013 | Timmons | ............ | G06F 19/3456 |
| | | | | 705/2 |
| 2014/0278495 A1* | 9/2014 | Rourke | ................. | G16H 10/60 |
| | | | | 705/2 |
| 2015/0161351 A1* | 6/2015 | Scalpati | ............. | G06F 19/3456 |
| | | | | 705/2 |
| 2016/0364547 A1* | 12/2016 | Love | ................... | G06F 19/3418 |
| 2017/0132393 A1* | 5/2017 | Natarajan | ............ | G06Q 10/087 |
| 2018/0032680 A1* | 2/2018 | Chen | ..................... | G16H 10/60 |
| 2018/0075215 A1* | 3/2018 | Loiacono | ................ | H04W 4/60 |
| 2019/0156938 A1* | 5/2019 | Brunner | ................. | G16H 40/20 |
| 2019/0370845 A1* | 12/2019 | Peysekhman | .......... | G16H 40/63 |

* cited by examiner

COMPUTING SYSTEM FOR GENERATING DELAYED ELECTRONIC PRESCRIPTIONS

BACKGROUND

Electronic health record applications (EHRs) are computer-executable applications utilized in healthcare environments. EHRs are generally configured to perform various tasks related to healthcare including patient intake tasks, insurance processing tasks, billing tasks, health record maintenance tasks, and so forth. Some EHRs have been configured with electronic prescription functionality, where an EHR can receive input from a healthcare worker causing the EHR to create an electronic prescription for a patient, and the EHR can be configured to direct the electronic prescription to a pharmacy specified by the healthcare worker and/or the patient. A device operated by the pharmacy (e.g., a computing device) can receive the electronic prescription from the EHR, and the device can notify a pharmacist at the pharmacy that the prescription is to be filled. The pharmacist may then fill the prescription.

When an EHR generates an electronic prescription for a controlled substance (e.g., a medication that has a high potential for abuse by a patient, such as a substance classified as being in schedules 2-5 by the United States Drug Enforcement Administration as of Feb. 13, 2018), the components of the prescription (e.g., identity of the medication, dosage information, pharmacy information, etc.) are typically immutable once set forth to the EHR. Thus, at the point of care, the patient must generally inform a healthcare worker prescribing the controlled substance as to which pharmacy is to be specified in the electronic prescription. A client EHR executing on a client computing operated by the healthcare worker may then receive input from the healthcare worker that is indicative of the components of the prescription (including an identity of a pharmacy), and the EHR can construct the electronic prescription and transmit the electronic prescription to a device operated by the pharmacy. However, the patient may not know which pharmacy he or she wishes to obtain the controlled substance from at the time of prescribing.

One approach to the above-identified problem is to configure the EHR to generate an incomplete electronic prescription that includes the necessary components of the prescription with the exception of the identity of the pharmacy. The EHR can then store the incomplete electronic prescription in a data store, and sometime later, the EHR can receive the identity of the pharmacy that the patient has selected to provide the controlled substance. The EHR can then generate a complete electronic prescription for the controlled substance. However, due to technological and regulatory factors, conventional EHR architectures are not amenable to generating an incomplete electronic prescription for a controlled substance. Additionally, electronic prescription workflows typically require electronic prescriptions to be electronically signed and verified within a short duration of time (e.g., a few minutes) after generation, which is not possible when the electronic prescription is incomplete. Extending the duration of time for the electronic prescription to be verified may increase the chance of unauthorized access of the electronic prescription and hence is undesirable.

SUMMARY

The following is a brief summary of subject matter that is described in greater detail herein. This summary is not intended to be limiting as to the scope of the claims.

Described herein are various technologies pertaining to electronic prescription generation. More specifically, an electronic health records application (EHR) is described herein, wherein the EHR is a distributed application that includes server-side functionality (server EHR) and client-side functionality (client EHR). A patient portal application is also described herein, wherein the patient portal application is a distributed application that includes server-side functionality (server patient portal application) and client-side functionality (client patient portal application). The EHR and the patient portal application can work in conjunction with one another to generate a delayed electronic prescription in which the EHR receives components of the prescription at different times and constructs an electronic prescription once all necessary components of the prescription are received by the EHR.

In operation, a client computing device executing the client EHR is operated by a healthcare worker providing care to a patient. The healthcare worker may decide to prescribe a medication (e.g., a controlled substance) to the patient. The client EHR may receive input from the healthcare worker, wherein the input is indicative of precursor data for an electronic prescription for the controlled substance. The precursor data is data that by itself is necessary, but not sufficient, for constructing an electronic prescription that can be filled by a pharmacy. For instance, the precursor data may include an identity of the patient, an identity of the healthcare worker, an identity of the controlled substance, a dosage amount of the controlled substance for the patient, refill information, an identity of the EHR, and an indication as to how often the patient is to consume the controlled substance. Notably, the precursor data may fail to include an identity of a pharmacy that is to provide the controlled substance in the prescription and an electronic signature for the healthcare worker prescribing the controlled substance. The server EHR may use the precursor data in connection with constructing the electronic prescription.

The client EHR may then transmit the precursor data to the server EHR executing on a first server computing device. The server EHR may cause the precursor data to be stored in a data store that is accessible to the server EHR. Further, the server EHR transmits the precursor data to a server patient portal application executing on a second server computing device, wherein the server patient portal application stores the precursor data in a data store accessible to the server patient portal application. The server patient portal application transmits a request for an identity of a pharmacy to a client patient portal application executing on a patient computing device operated by the patient. For instance, the patient computing device may be a mobile computing device operated by the patient.

Subsequent to receiving the request, the client patient portal application presents the request in a graphical user interface (GUI) for the client patient portal application, wherein the GUI is displayed on a display of the patient computing device. The patient may then review the request, and the client patient portal application can receive (via the GUI) a selection of an identity of a pharmacy that is to receive the electronic prescription for the controlled substance. Responsive to receiving the selection of the identity of the pharmacy, the client patient portal application transmits the identity of the pharmacy to the server patient portal application, wherein the server patient portal application can store the identity of the pharmacy in the data store in association with the precursor data.

Subsequently, the server patient portal application transmits the precursor data and the identity of the pharmacy to the server EHR. The server EHR may then transmit a notification to the client EHR (executing on the client computing device or another client computing device by way of which the healthcare worker has authenticated with the server EHR), wherein the notification indicates that the patient has selected a pharmacy that is to provide the controlled substance identified in the electronic prescription, wherein the notification comprises the precursor data and the identity of the pharmacy. The healthcare worker then reviews the notification. The client EHR then receives authorization credentials for the healthcare worker as input from the healthcare worker, and transmits the authorization credentials to the server EHR, wherein the authorization credentials indicate that the healthcare worker approves the (finalized) prescription. The authorization credentials may include multi-factor authentication credentials, for instance, two-factor authentication credentials. Responsive to receiving the authorization credentials, the server EHR constructs the electronic prescription using the precursor data, the identity of the pharmacy, and an electronic signature for the healthcare worker.

The server EHR then transmits the electronic prescription to a hub application executing on a hub computing system. The hub application may verify the integrity of the electronic prescription using the electronic signature in the electronic prescription. The hub computing system then transmits the electronic prescription to a computing system operated by the pharmacy, wherein the computing system can present the electronic prescription to a pharmacist at the pharmacy. The pharmacist may then then fill the prescription.

The above-described technologies present various advantages over conventional electronic prescription generation technologies. First, the above-described technologies enable an EHR to construct a prescription for a controlled substance that is to be sent to a pharmacy selected by the patient subsequent to a patient encounter with a healthcare worker while still retaining the electronic security measures required for electronic prescriptions of controlled substances. Second, the above-described technologies are compatible with existing EHR architectures and thus do not require EHR retooling in order to function. Third, the above-described technologies do not require extending the duration of time for which the electronic prescription must be verified.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Various technologies pertaining to generating an electronic prescription are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Figure 1:
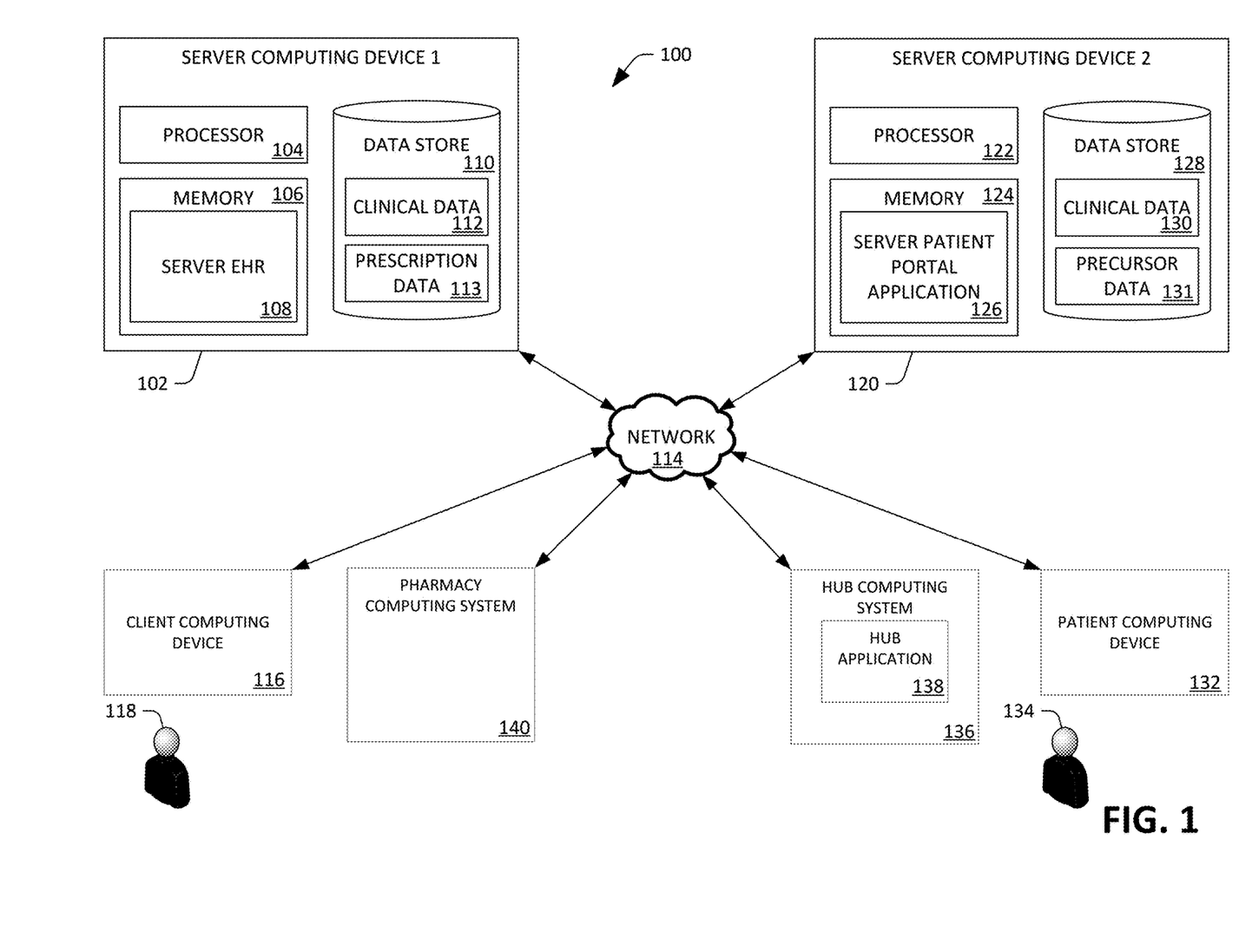
FIG. 1 is a functional block diagram of an exemplary computing system that facilitates generating a delayed electronic prescription.

With reference to FIG. 1, an exemplary computing system 100 that facilitates generating an electronic prescription is illustrated. The computing system 100 includes a first server computing device 102. The first server computing device 102 comprises a processor 104 and memory 106, wherein the memory 106 has a server electronic health records application (server EHR) 108 loaded therein. The server EHR 108 is generally configured to perform a variety of tasks related to patient healthcare in a healthcare facility (e.g., patient intake, prescription generation, patient record creation and maintenance, etc.). The first server computing device 102 also includes a data store 110 that comprises clinical data 112 (amongst other data) about patients, wherein the clinical data 112 is maintained by the server EHR 108. The clinical data 112 can include electronic health records, prescription records, claims data, patient/disease registries data, health surveys data, and/or clinical trials data. The data store 110 may additionally comprise prescription data 113, wherein the prescription data 113 includes electronic prescriptions for patients. In an embodiment, the data store 110 may comprise precursor data for an electronic prescription for a controlled substance for a patient (described in greater detail below).

Figure 2:
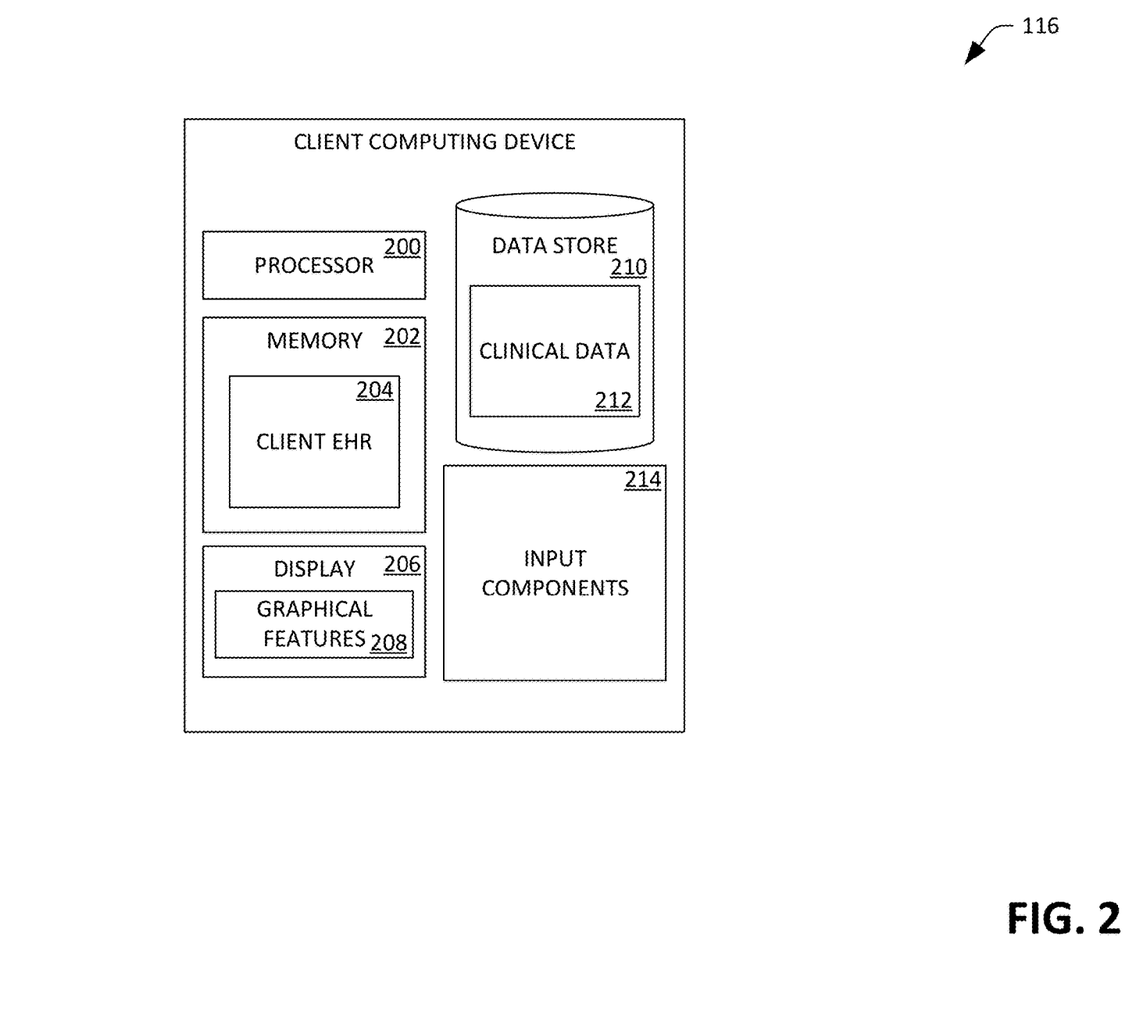
FIG. 2 is a functional block diagram of an exemplary client computing device.

The computing system 100 also includes a client computing device 116 operated by a healthcare worker 118. In an embodiment, the client computing device 116 can be a mobile computing device, such as a tablet computing device. The client computing device 116 is in communication with the first server computing device 102 by way of a network 114 (e.g., the Internet, intranet). Turning briefly now to FIG. 2, the client computing device 116 includes a processor 200 and memory 202, wherein the memory 202 has a client electronic health records application (client EHR) 204 loaded therein. In general, the client EHR 204 is configured to interface with the server EHR 108 executing on the first server computing device 102, thereby providing the healthcare worker 118 with access to functionality of the server EHR 108.

The client computing device 116 may also include a data store 210 comprising clinical data 212 about patients. It is understood that there may be overlap between the clinical data 212 stored in the data store 210 and the clinical data 112 stored in the data store 110. The client computing device may include a display 206, wherein graphical features 208 may be presented thereon. Furthermore, the client computing device 116 may include input components 214 (e.g., mouse, keyboard, touchscreen, microphone, etc.) suitable for data input.

Turning back to FIG. 1, the computing system 100 includes a second server computing device 120 that is in communication with the first server computing device 102 by way of the network 114. The second server computing device 120 comprises a processor 122 and memory 124, wherein the memory 124 has a server patient portal application 126 loaded therein. The server patient portal application 126 is configured to allow a patient 134 to access his or her health data, including prescription medications, health records, communication with healthcare providers, input-self reported patient health data, etc. The patient 134 may interface with the server patient portal application 126 by way of a patient computing device 132 (described below).

The second server computing device 120 may include a data store 128. The data store 128 may comprise clinical data 130 for patients, wherein the clinical data 130 is a subset of the clinical data 112 maintained by the server EHR 108. Thus, the server EHR 108 is configured to provide the server patient portal application 126 with the clinical data 112, wherein an administrator (not shown) of the server EHR 108 can set forth policies as to what data is included in the clinical data 130 (and the format of such data). In addition, the patient portal application 126 can maintain data provided directly by the patient 134 to the server patient portal application 126.

The data store 128 may also include precursor data 131 for an electronic prescription for a controlled substance. In general, the precursor data 131 includes data that is necessary, but not sufficient, for construction of an electronic prescription for a controlled substance. For instance, the precursor data 131 may include an identity of the patient 134, an identity of the healthcare worker 118, an identity of a medication (e.g., the controlled substance), a dosage amount of the controlled substance for the patient 134, an indication as how often the patient 134 is to consume the controlled substance, an identity of the server EHR 108, and/or information regarding refills of the controlled substance. Likewise, the precursor data 131 may fail to include an identity of a pharmacy that is to provide the controlled substance and an electronic signature for the healthcare worker 118 that is to prescribe the controlled substance. The precursor data 131 may also fail to include a date that is to be included in the electronic prescription.

Figure 3:
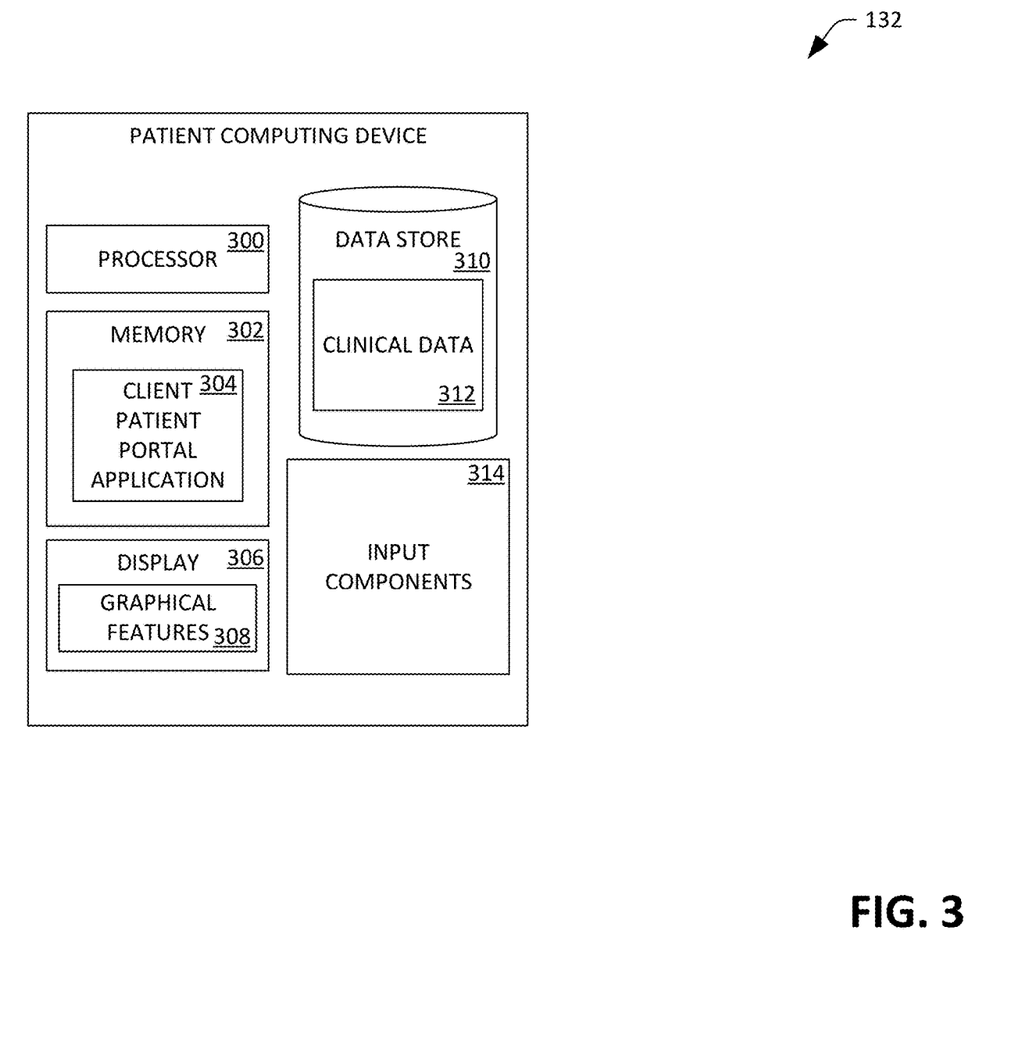
FIG. 3 is a functional block diagram of an exemplary patient computing device.

The computing system 100 additionally includes a patient computing device 132 operated by the patient 134. In an embodiment, the patient computing device 132 can be a mobile computing device, such as a tablet computing device, a wearable computing device (e.g., a smartwatch), or a smartphone. The patient computing device 132 may also be a desktop computing device or a laptop computing device. The patient computing device 132 is in communication with the second server computing device 120 by way of the network 114. Referring briefly now to FIG. 3, the patient computing device 132 includes a processor 300 and memory 302, wherein the memory 302 has a client patient portal application 304 loaded therein. In general, the client patient portal application 304 is configured to interface with the server patient portal application 126 to allow the patient 134 to access his or her health data that is maintained by the server patient portal application 126.

The patient computing device 132 may also include a data store 310 comprising clinical data 312 (as well as other data) about the patient 134. The patient computing device 132 may include a display 306, wherein graphical features 308 may be presented thereon. Furthermore, the patient computing device 132 may include input components 314 (e.g., mouse, keyboard, touchscreen, microphone, etc.) suitable for data input.

The computing system 100 may additionally include a hub computing system 136. The hub computing system 136 comprises a processor (not shown) and memory (not shown), wherein the memory has a hub application 138 loaded therein. The hub computing system 136 may be referred to as a transaction hub and may be in communication with the first server computing device 102, the pharmacy computing system 140, and optionally, a computing system operated by an insurance company. In general, the hub application 138 is configured to route an electronic prescription transmitted from the server EHR 108 to a pharmacy computing system (described below) operated by a pharmacy. For instance, the hub computing system 136 may maintain a master list of pharmacies, and the hub application 138 may route an electronic prescription to the pharmacy identified in the electronic prescription using the master list of pharmacies. The hub application 138 may also be configured to obtain approvals from insurance companies for electronic prescriptions for patients. Additionally, the hub application 138 may be configured to verify that an electronic prescription has not been tampered with using an electronic signature in the electronic prescription.

The computing system also includes a pharmacy computing system 140 maintained by a pharmacy. The pharmacy computing system 140 is in communication with the hub computing system 136 by way of the network 114. The pharmacy computing system 140 may be located at a pharmacy.

Exemplary operation of the computing system 100 is now set forth. It is contemplated that the healthcare worker 118 has had a patient encounter with the patient 134 and that the healthcare worker 118 has decided to prescribe a controlled substance to the patient 134. The client computing device 116 can receive user credentials from the healthcare worker 118, and can transmit the user credentials to the first server computing device 102. The server EHR 108 can authenticate the healthcare worker 118 based upon the user credentials, and can provide the healthcare worker 118 with access to the functionality of the server EHR 108 via the client EHR 204 executing on the client computing device 116.

The client EHR 204 may then receive precursor data as input from the healthcare worker 118. The client EHR 204 may then transmit the precursor data to the server EHR 108 executing on the first server computing device 102. The precursor data is data that by itself is necessary, but not sufficient, for generating an electronic prescription for a controlled substance. For instance, the precursor data may include an identity of the patient, an identity of the healthcare worker, an identity of the controlled substance, a dosage amount of the controlled substance for the patient, refill information, an identity of the server EHR 108, and an indication as to how often the patient is to consume the controlled substance. Notably, the precursor data may fail to include an identity of a pharmacy that is to fill the prescription and an electronic signature for the healthcare worker that is required by a pharmacy in order to fill the prescription. The precursor data may also fail to include a date on which the electronic prescription is generated. The client EHR 204 may then transmit the precursor data to the server EHR 108.

Responsive to receiving the precursor data from the client EHR 204, the server EHR 108 transmits the precursor data to the server patient portal application 126 executing on the second server computing device 120. The server patient portal application 126 then stores the precursor data in the data store 128 as the precursor data 131. It is to be appreciated that the server EHR 108 may or may not retain the precursor data for the electronic prescription in the data store 110. However, it is also to be appreciated that the server patient portal application 126 may retain the precursor data in the data store 128 indefinitely.

Subsequently, the server patient portal application 126 transmits a request for an identity of a pharmacy that is to provide the controlled substance identified in the precursor data to the client patient portal application 304 executing on the patient computing device 132. The request may include the identity of the controlled substance. The client patient portal application 304 can then present the request to the patient 134. For instance, the client patient portal application 304 can present the request on the display 306. The client patient portal application 304 may then receive an identity of a pharmacy that is to provide the controlled substance as input from the patient 134. The client patient portal application 304 can then transmit the identity of the pharmacy to the server patient portal application 126, wherein the client patient portal application can store the identity of the pharmacy in association with the precursor data 131 in the data store 128.

In an embodiment, the server patient portal application 126 may also transmit a request for insurance information for the patient to the client patient portal application 304. The client patient portal application 304 can then present the request for insurance information to the patient 134. For instance, the client patient portal application 304 can present the request on the display 306. The client patient portal application 304 may then receive the insurance information as input from the patient 134 and transmit the insurance information to the server patient portal application 126.

In an embodiment, the server patient portal application 126 maintains a list of identities for pharmacies that have attributes that are desirable by the patient 134 (e.g., located in an area near a residence of the patient 134, low prices for medications, high customer ratings, etc.) In the embodiment, the server patient portal application 126 transmit identities of pharmacies in the list to the client patient portal application 304 along with the request for the identity of the pharmacy. The client patient portal application 304 can then present the identities within a GUI presented on the display 306. The GUI can then receive a selection of an identity of a pharmacy in the identities from the patient 134. The client patient portal application 304 can then transmit the identity of the pharmacy to the server patient portal application 126, wherein the client patient portal application can store the identity of the pharmacy in association with the precursor data 131 in the data store 128.

Subsequent to receiving the identity of the pharmacy (and optionally the insurance information) and storing the identity of the pharmacy in association with the precursor data 131, the server patient portal application 126 can retrieve the precursor data 131 and the identity of the pharmacy from the data store 128. In an example, the server patient portal application 126 can retrieve the precursor data 131 and the identity of the pharmacy from the data store 128 responsive to receiving an indication from the server EHR 108 that the healthcare worker 118 has logged into the EHR. In another example, responsive to receiving the identity of the pharmacy, the server patient portal application 126 may ascertain that the healthcare worker 118 is logged into the EHR, and the server patient portal application 126 may retrieve the precursor data 131 and the identity of the pharmacy from the data store 128 responsive to determining that the healthcare worker 118 is logged into the EHR. The server patient portal application 126 can then transmit the identity of the pharmacy, the precursor data to the server EHR 108, and optionally, the insurance information to the server EHR 108.

The server EHR 108 may then transmit a notification to the client EHR 204 indicating that the patient 134 has a selected a pharmacy that is to provide the controlled substance. The notification may comprise the precursor data, the identity of the pharmacy, and optionally, the insurance information. The client EHR 204 may present the notification on the display 206, whereupon the healthcare worker 118 may review the notification. The healthcare worker 118 may then decide to electronically sign the prescription, and as such the client EHR 204 may receive authorization credentials for the healthcare worker 118 as input from the healthcare worker 118. The authorization credentials may include multi-factor authorization credentials. For example, the authorization credentials may include a username and password, as well as a one-time password generated from a hardware or software-based token generator. In another example, the authorization credentials may include a username and password, as well as a biometric factor of the healthcare worker 118 (e.g., a fingerprint scan of the healthcare worker 118).

The server EHR 108 may then construct the electronic prescription using the precursor data, the identity of the pharmacy, and an electronic signature for the healthcare worker 118. The server EHR 108 may execute a hash function over the electronic prescription to produce a hash for the electronic prescription. The server EHR 108 may then include the hash in the electronic signature for the healthcare worker 118. The server EHR 108 may also include a date on which the electronic prescription was signed in the electronic prescription. In an embodiment, the hash function may employ a private cryptographic key for the healthcare worker 118.

Responsive to constructing the electronic prescription, the server EHR 108 transmits the electronic prescription to the hub application 138 executing on the hub computing system 136. The server EHR 108 may also transmit insurance information for the patient 134. The hub application 138 may then verify the integrity of the contents of the electronic prescription using the electronic signature in the electronic prescription. For instance, the hub application 138 may execute the hashing function over the contents of the electronic prescription to generate a second hash. The hub application 138 may then compare the second hash to the hash in the electronic signature. In the event that the hashes do not match, the hub application 138 may identify the prescription as having been tampered with and can fail to transmit the prescription to the pharmacy computing system 140. The hub application 138 may also transmit a message to the server EHR 108 indicating that the electronic prescription has undergone tampering. Additionally, the hub application 138 may also obtain approval for the electronic prescription by communicating with a computing system operated by an insurance company identified in the insurance information.

In an embodiment where the hash function employs a private cryptographic key for the healthcare worker 118, the hub computing application 138 may store a public cryptographic key in a data store of the hub computing system 136. The hub application 138 may utilize the public key and the private key in order to verify that the electronic prescription has not undergone tampering.

The hub application 138 may then route the electronic prescription, by way of the network 114, to the pharmacy computing system 140 for the pharmacy identified in the electronic prescription. The pharmacy computing system 140 may then present the electronic prescription to a pharmacist at the pharmacy, and the pharmacist can fill the prescription.

In an embodiment, subsequent to transmitting the electronic prescription to the hub application 138, the server EHR 108 may transmit a notification to the server patient portal application 126 indicating that the server EHR 108 has transmitted the electronic prescription to the pharmacy computing system 140 (by way of the hub computing system 136). The server patient portal application 126 may then forward the notification to the patient computing device 132, wherein the patient computing device 132 can present the notification to the patient 134 on the display 306 of the patient computing device 132.

In an embodiment, the server patient portal application 126 may be configured to retain the precursor data for a time duration (e.g., one week, two weeks etc.). In the embodiment, if the server patient portal application 126 does not receive an identity of a pharmacy within the time duration, the server patient portal application 126 may cause the above-described process to fail to execute. The server patient portal application 126 may also transmit a message to the server EHR 108 and the client patient portal application 126 indicating that the server patient portal application 126 has not received an identity of a pharmacy that is to provide the controlled substance from the client patient portal application 304.

In another embodiment, the server patient portal application 126 may be configured to receive an identity of a default (or suggested) pharmacy from the server EHR 108 along with a time duration. For instance, the client computing device 116 can receive input indicative of the identity of the default pharmacy from the healthcare worker 118 (e.g., at the time of a patient encounter between the healthcare worker 118 and the patient 134). The client computing device 116 can then transmit the identity of the default pharmacy to the server EHR 108. The server EHR 108 can then transmit the identity of the default pharmacy to the server patient portal application 126, whereupon the server patient portal application 126 can retain the identity of the default pharmacy. If the server patient portal application 126 does not receive an identity of a pharmacy from the client patient portal application 304 within the time duration (described above), the server patient portal application 126 may transmit the identity of the default pharmacy to the server EHR 108, and the server EHR 108 may construct and transmit the electronic prescription as detailed above using the identity of the default pharmacy. If the server patient portal application 126 does receive an identity of a pharmacy from the client patient portal application 304 within the time duration, the server patient portal application 126 will transmit the identity of the pharmacy to the server EHR 108, which will then use the identity of the pharmacy in constructing and transmitting the electronic prescription, thus effectively overriding the choice of the default pharmacy. It is understood that the identity of the default pharmacy and the identity of the pharmacy received from the client patient portal application 304 may be the same.

While the above-described functionality has been described as being performed using the server EHR 108, other possibilities are contemplated. In an embodiment, the above-described functionality may be accomplished through use of a prescription module that can be incorporated into an EHR. In another embodiment, the above-described functionality may be primarily accomplished through a use of a prescription application that executes on a computing device that is in network communication with the first server computing device 102.

Figure 4:
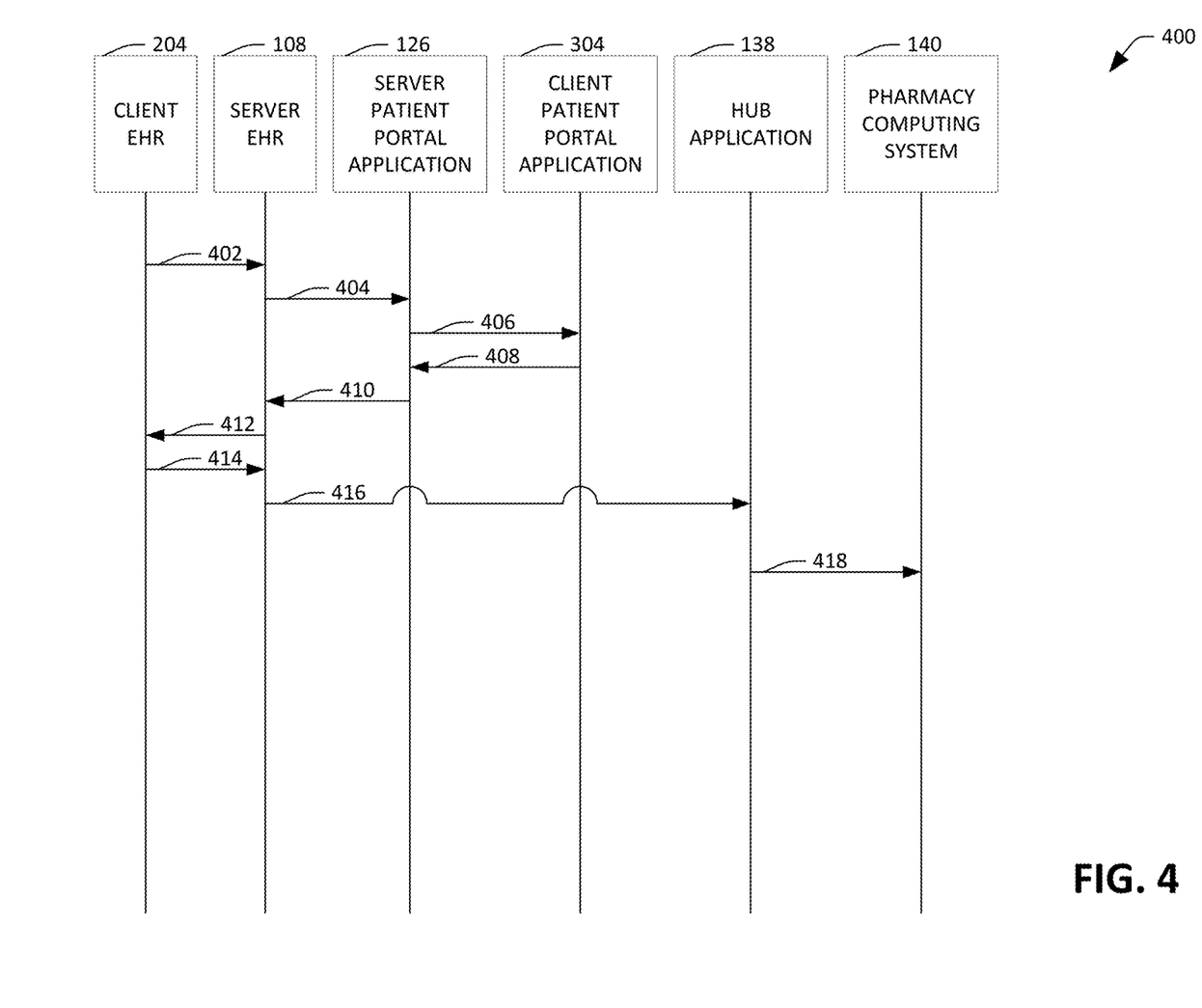
FIG. 4 illustrates a control flow diagram for generating a delayed electronic prescription.

With reference now to FIG. 4, an exemplary control flow diagram 400 is illustrated. At 402, the client EHR 204 receives input from a healthcare worker causing the client EHR 204 to transmit precursor data for an electronic prescription for a patient to the server EHR 108. The electronic prescription may be for a controlled substance. The precursor data may include some, but not all, of components required to generate the electronic prescription. For instance, the precursor data may fail to include an identity of a pharmacy that is to fill the prescription. At 404, responsive to receiving the precursor data from the client EHR 204, the server EHR 108 transmits the precursor data to the server patient portal application 126, wherein the server patient portal application 126 causes the precursor data to be stored in the data store 128.

At 406, the server patient portal application 126 transmits a request for an identity of a pharmacy to the client patient portal application 304 executing on the patient computing device 132. Optionally, the server patient portal application 126 may also transmit a request for insurance information for the patient to the client patient portal application 304. Subsequently, at 408, the client patient portal application 304 transmits an identity of a pharmacy that is to provide the controlled substance to the server patient portal application 126 responsive to receiving a selection of the identity of the pharmacy from the patient. Optionally, the client patient portal application 308 may also transmit insurance information for the patient to the server patient portal application 126. At 410, the server patient portal application 126 transmits the identity of pharmacy and the precursor data to the server EHR 108.

At 412, responsive to receiving the identity of the pharmacy and the precursor data, the server EHR 108 transmits a notification to the client EHR 204 indicating that the patient has selected the pharmacy that is to provide the controlled substance. The healthcare worker 118 may review the notification, and the client EHR 204 may receive authorization credentials for the healthcare worker 118 as input from the healthcare worker 118. The authorization credentials may include two-factor authorization credentials (described above). At 414, the client EHR 204 transmits the authorization credentials for the healthcare worker to the server EHR 108. The server EHR 108 then constructs the electronic prescription using the precursor data and the identity of the pharmacy and electronically signs the electronic prescription to generate an electronic prescription using an electronic signature of the healthcare worker 118. At 416, the server EHR 108 transmits the electronic prescription to the hub application 138. The hub application may then verify the contents of the electronic prescription based upon the electronic signature for the healthcare worker 118 in the electronic prescription. At 418, after verifying the contents of the electronic prescription, the hub application 138 routes the electronic prescription to the pharmacy computing system 140 based on the identity of the pharmacy in the electronic prescription.

Figure 5:
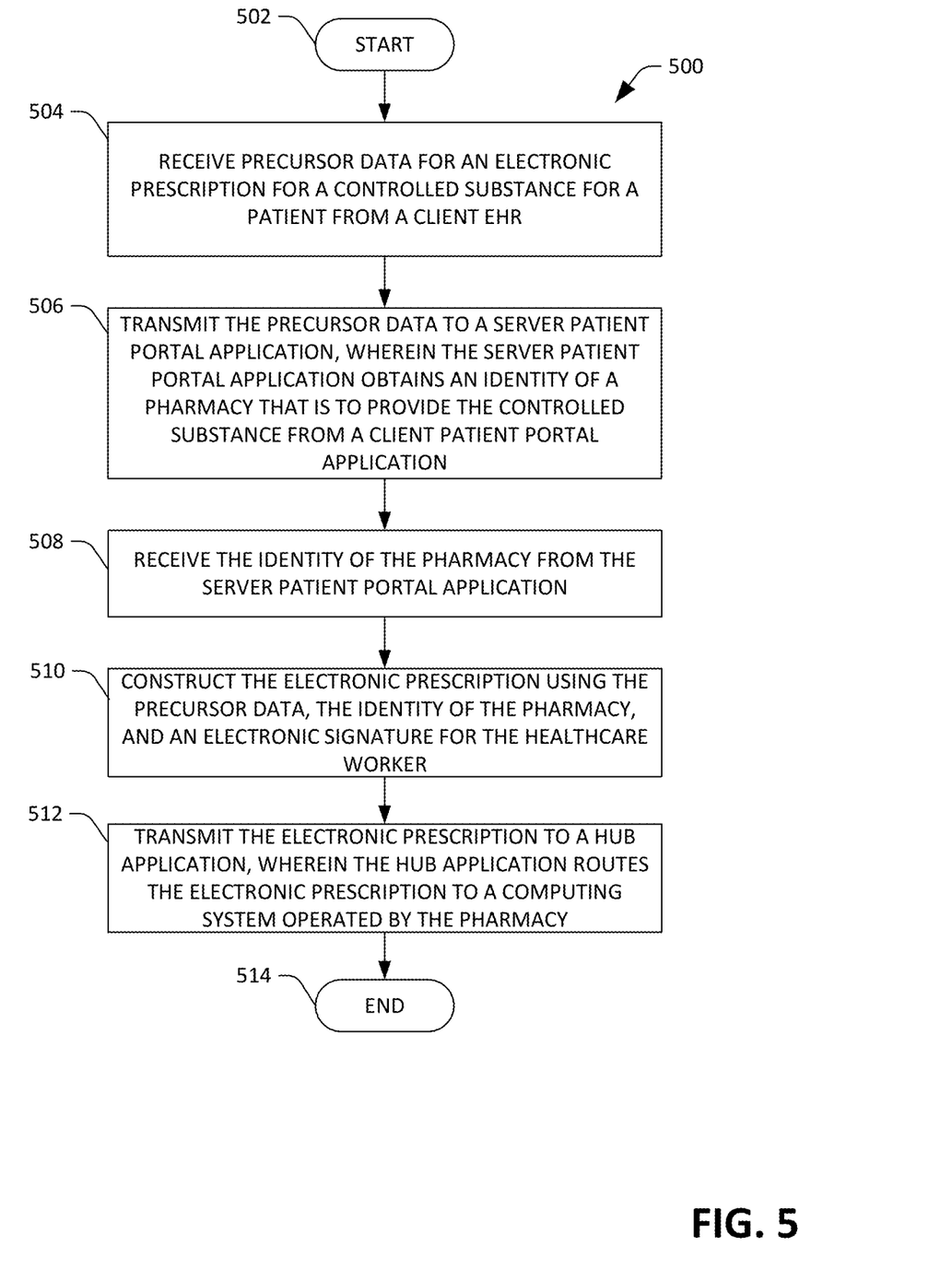
FIG. 5 is an exemplary methodology executed by a server electronic health records application (server EHR) for generating a delayed electronic prescription.
Figure 6:
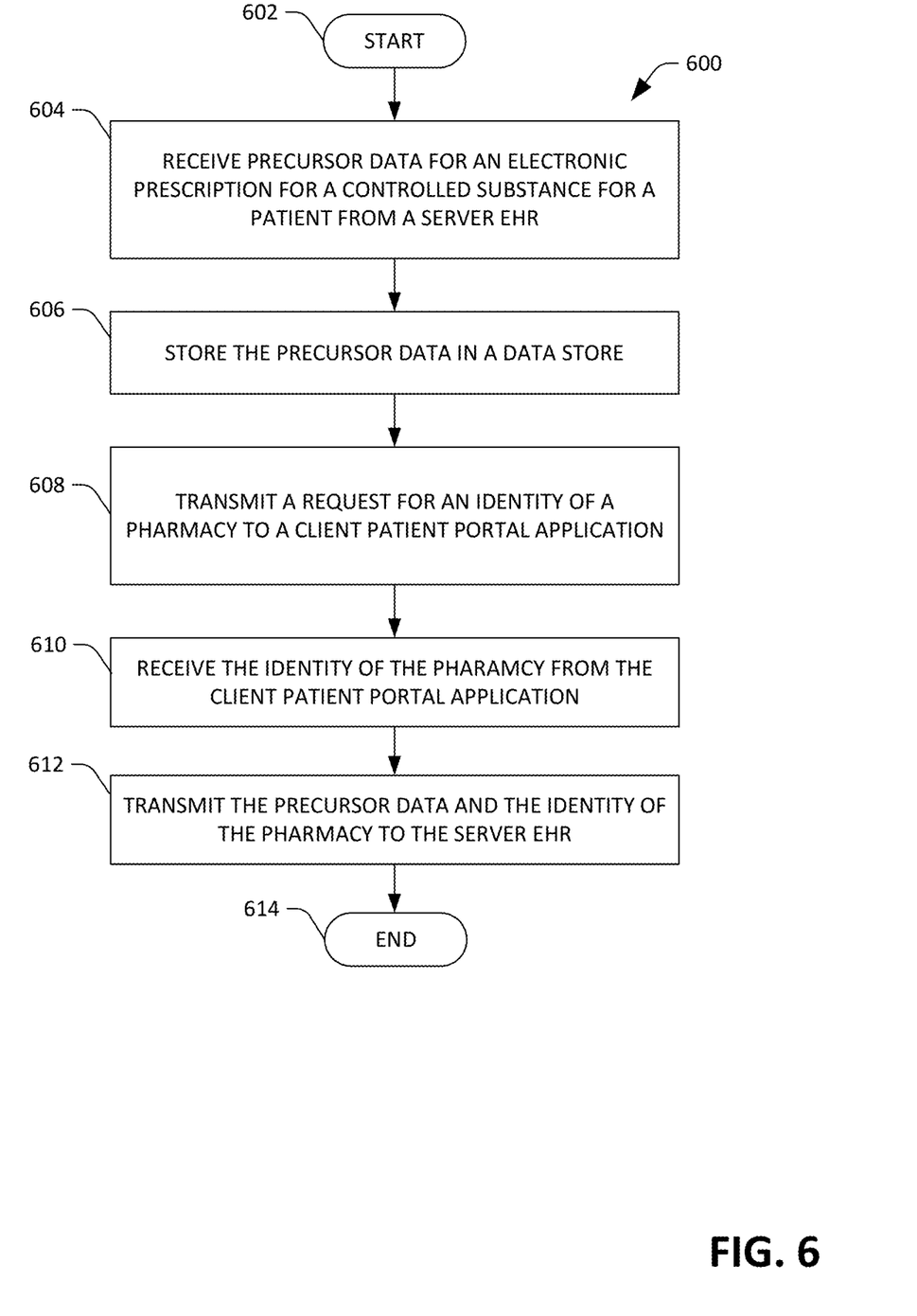
FIG. 6 is an exemplary methodology executed by a server patient portal application for generating a delayed electronic prescription.

FIGS. 5 and 6 illustrate exemplary methodologies relating to constructing an electronic prescription from precursor data. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 5, a methodology 500 performed by a server EHR executing on a server computing device that facilitates generating a delayed electronic prescription is illustrated. The methodology 500 begins at 502, and at 504 the server EHR receives precursor data by way of a network for an electronic prescription for a controlled substance for a patient from a client computing device. The client computing device is operated by a healthcare worker. The precursor data may fail to include an identity of a pharmacy that is to provide the controlled substance. At 506, responsive to receiving the precursor data, the server EHR transmits the precursor data by way of the network to a server patient portal application executing on a second server computing device. The server patient portal application stores the precursor data in a data store of the second server computing device. The server patient portal application also obtains, by way of the network, an identity of a pharmacy that is to provide the controlled substance from a client patient portal application executing on a patient computing device operated by the patient.

Subsequently, at 508, the server EHR receives the precursor data and the identity of the pharmacy from the server patient portal application. At 510, the server EHR constructs the electronic prescription using the precursor data, the identity of the pharmacy, and an electronic signature for the healthcare worker. At 512, responsive to constructing the electronic prescription, the server EHR transmits the electronic prescription by way of the network to a hub application executing on a hub computing system, wherein the hub application causes the electronic prescription to be routed to a computing system operated by the pharmacy based on the identity of the pharmacy included in the electronic prescription. The methodology 500 concludes at 514.

Turning now to FIG. 6, a methodology 600 executed by a server patient portal application executing on a second server computing device that facilitates generating a delayed electronic prescription is illustrated. The methodology 600 begins at 602, and at 604, the server patient portal application receives precursor data for an electronic prescription for a controlled substance for a patient by way of a network from a server EHR executing on a server computing device. The precursor data may fail to include an identity of a pharmacy that is to provide the controlled substance. At 606, responsive to receiving the precursor data, the server patient portal application stores the precursor data for the prescription in a data store of the second server computing device. At 608, the server patient portal application transmits a request for an identity of a pharmacy that is to provide the controlled substance by way of the network to a patient computing device operated by the patient.

Subsequently, at 610, the server patient portal application receives the identity of the pharmacy that is to provide the controlled substance from the patient computing device. The server patient portal application may store the identity of the pharmacy in association with the precursor data in the data store. At 612, subsequent to receiving the identity of the pharmacy, the server patient portal application transmits the precursor data and the identity of the pharmacy to the server EHR. The server EHR then causes an electronic prescription for the controlled substance to be generated. The server EHR also causes the electronic prescription to be received by a computing device operated by the pharmacy. The methodology 600 concludes at 614.

Figure 7:
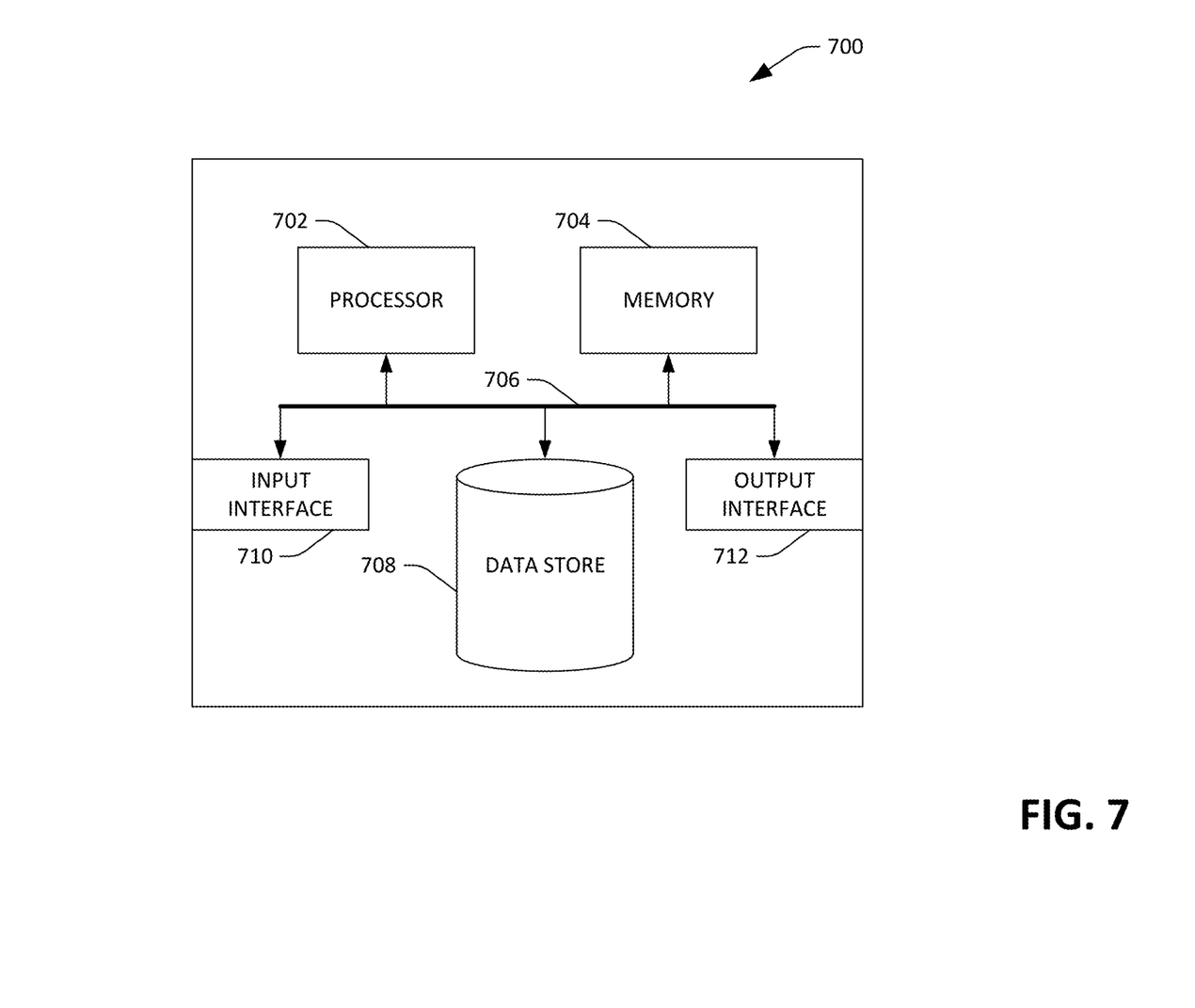
FIG. 7 is an exemplary computing system.

Referring now to FIG. 7, a high-level illustration of an exemplary computing device 700 that can be used in accordance with the systems and methodologies disclosed herein is illustrated. For instance, the computing device 700 may be used in a system that constructs a delayed electronic prescription for a controlled substance. By way of another example, the computing device 700 can be used in a system that receives and stores precursor data for a delayed electronic prescription for a controlled substance. The computing device 700 includes at least one processor 702 that executes instructions that are stored in a memory 704. The instructions may be, for instance, instructions for implementing functionality described as being carried out by one or more components discussed above or instructions for implementing one or more of the methods described above. The processor 702 may access the memory 704 by way of a system bus 706. In addition to storing executable instructions, the memory 704 may also store precursor data for electronic prescriptions, electronic prescriptions, etc.

The computing device 700 additionally includes a data store 708 that is accessible by the processor 702 by way of the system bus 706. The data store 708 may include executable instructions, precursor data for electronic prescriptions, electronic prescriptions, etc. The computing device 700 also includes an input interface 710 that allows external devices to communicate with the computing device 700. For instance, the input interface 710 may be used to receive instructions from an external computer device, from a user, etc. The computing device 700 also includes an output interface 712 that interfaces the computing device 700 with one or more external devices. For example, the computing device 700 may display text, images, etc. by way of the output interface 712.

It is contemplated that the external devices that communicate with the computing device 700 via the input interface 710 and the output interface 712 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 700 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 700 may be a distributed system. Thus, for instance, several devices may be in communication by way of a network connection and may collectively perform tasks described as being performed by the computing device 700.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A server computing device comprising:
a processor; and
memory storing a server electronic health records application (server EHR), that, when executed by the processor, causes the processor to perform acts comprising:
receiving precursor data for an electronic prescription for a controlled substance for a patient that is to be constructed, wherein the precursor data is received over a first network connection from a client electronic health records application (client EHR), wherein the client EHR is executing on a client computing device operated by a healthcare worker, wherein the precursor data is useable by the server EHR in connection with constructing the electronic prescription for the controlled substance, the precursor data includes an identity of the controlled substance and an identity of the patient, the precursor data fails to include an identity of a pharmacy;
responsive to receiving the precursor data, transmitting the precursor data over a second network connection to a server patient portal application executing on a second server computing device, wherein the precursor data is retained by the server patient portal application in a computer-readable data store accessible to the server patient portal application, wherein upon transmitting the precursor data to the server patient portal application, the server EHR discards the precursor data from computer-readable storage of the server EHR such that the precursor data is no longer accessible to the server EHR on the computer-readable storage, wherein the identity of the pharmacy is obtained by the server patient portal application from a client patient portal application executing on a patient computing device operated by the patient;
subsequent to discarding the precursor data from the computer-readable storage of the server EHR, receiving the precursor data and the identity of the pharmacy from the server patient portal application over the second network connection;
subsequent to receiving the precursor data and the identity of the pharmacy from the server patient portal application, constructing the electronic prescription using the precursor data, the identity of the pharmacy, and an electronic signature for the healthcare worker; and
causing the electronic prescription to be transmitted over a third network connection to a computing system operated by the pharmacy.

2. The server computing device of claim 1, wherein the precursor data further includes:
   an identity of the healthcare worker;
   a dosage amount of the controlled substance for the patient; and
   an indication as to how often the patient is to consume the controlled substance.

3. The server computing device of claim 1, the acts further comprising:
   responsive to constructing the electronic prescription, transmitting the electronic prescription over the third network connection to a hub application executing on a hub computing system, wherein the electronic prescription is routed by the hub application to the computing system operated by the pharmacy based on the identity of the pharmacy in the electronic prescription.

4. The server computing device of claim 3, wherein integrity of the electronic prescription is verified by the hub application based upon the electronic signature in the electronic prescription.

5. The server computing device of claim 3, the acts further comprising:
   transmitting, over the second network connection, a notification to the server patient portal application indicating that the electronic prescription has been transmitted to the computing system operated by the pharmacy, wherein the notification is forwarded by the server patient portal application to the patient computing device.

6. The server computing device of claim 1, wherein constructing the electronic prescription comprises:
   transmitting, over the first network connection, a notification to the client EHR indicating that the patient has selected the pharmacy to provide the controlled substance, the notification comprising the precursor data and the identity of the pharmacy, wherein authorization credentials for the healthcare worker are received by the client EHR, and further wherein the authorization credentials are transmitted by the client EHR over the first network connection to the server EHR; and
   subsequent to receiving the authorization credentials for the healthcare worker from the client EHR, constructing the electronic prescription.

7. The server computing device of claim 1, wherein the electronic prescription further comprises a date on which constructing the electronic prescription occurred.

8. The server computing device of claim 1, wherein the patient computing device is a mobile computing device.

9. The server computing device of claim 1, wherein identities of pharmacies are transmitted over a fourth network connection by the server patient portal application to the client patient portal application, the identity of the pharmacy included in the identities of the pharmacies, wherein the identities of the pharmacies are displayed by the client patient portal application on a display of the patient computing device, wherein the identity of the pharmacy is transmitted over the fourth network connection by the client patient portal application to the server patient portal application responsive to receiving a selection of the identity of the pharmacy from the patient.

10. A method performed by a processor of a server computing device while the processor executes a server electronic health records application (server EHR), the method comprising:
   receiving precursor data for an electronic prescription for a controlled substance for a patient that is to be constructed, wherein the precursor data is received over a first network connection from a client electronic health records application (client EHR), wherein the client EHR is executing on a client computing device operated by a healthcare worker, wherein the precursor data usable by the server EHR in connection with constructing the electronic prescription for the controlled substance, the precursor data includes an identity of the controlled substance and an identity of the patient, the precursor data fails to include an identity of a pharmacy;
   responsive to receiving the precursor data, transmitting the precursor data over a second network connection to a server patient portal application executing on a second server computing device, wherein the precursor data is retained by the server patient portal application in a computer-readable data store accessible to the server patient portal application, wherein upon transmitting the precursor data to the server patient portal application, the server EHR discards the precursor data from computer-readable storage of the server EHR such that the precursor data is no longer accessible to the server EHR on the computer-readable storage, wherein a request for the identity of the pharmacy is transmitted over a third network connection by the server patient portal application to a client patient portal application executing on a patient computing device operated by the patient, wherein input is received by the client patient portal application from the patient causing the identity of the pharmacy to be received by the server EHR;
   subsequent to discarding the precursor data from the computer-readable storage of the server EHR, receiving the precursor data and the identity of the pharmacy from the server patient portal application over the second network connection;
   subsequent to receiving the precursor data and the identity of the pharmacy from the server patient portal application, constructing the electronic prescription using the precursor data, the identity of the pharmacy, and an electronic signature for the healthcare worker; and
   responsive to constructing the electronic prescription, transmitting the electronic prescription over a fourth network connection to a hub application executing on a hub computing system, wherein the electronic prescription is routed by the hub application to a computing system operated by the pharmacy based on the identity of the pharmacy in the electronic prescription.

11. The method of claim 10, wherein integrity of the electronic prescription is verified by the hub application based upon the electronic signature in the electronic prescription.

12. The method of claim 10, wherein the precursor data further includes:
   an identity of the healthcare worker;
   a dosage amount of the controlled substance for the patient an identity of the server EHR; and
   an indication as to how often the patient is to consume the controlled substance.

13. The method of claim 10, wherein the patient computing device is a mobile computing device.

14. The method of claim 10, wherein constructing the electronic prescription comprises:
   transmitting, over the first network connection, a notification to the client EHR indicating that the patient has selected the pharmacy to provide the controlled substance, the notification comprising the precursor data and the identity of the pharmacy, wherein authorization credentials for the healthcare worker are received by the client EHR, and further wherein the authorization credentials are transmitted by the client EHR over the first network connection to the server EHR; and subsequent to receiving the authorization credentials for the healthcare worker from the client EHR, constructing the electronic prescription.

15. A non-transitory computer-readable storage medium comprising a server electronic health records application (server EHR) that, when executed by a processor of a server computing device, causes the processor to perform acts comprising:

receiving precursor data for an electronic prescription for a controlled substance for a patient that is to be constructed, wherein the precursor data is received over a first network connection from a client electronic health records application (client EHR), wherein the client EHR is executing on a client computing device operated by a healthcare worker, wherein the precursor data is usable by the server EHR in connection with constructing the electronic prescription for the controlled substance, the precursor data includes an identity of the controlled substance and an identity of the patient, the precursor data fails to include an identity of a pharmacy;

responsive to receiving the precursor data, transmitting the precursor data over a second network connection to a server patient portal application executing on a second server computing device, wherein the precursor data is retained in a computer-readable data store accessible to the server patient portal application, wherein upon transmitting the precursor data to the server patient portal application, the server EHR discards the precursor data from computer-readable storage of the server EHR on the computer-readable storage such that the precursor data is no longer accessible to the server EHR, wherein a request for the identity of the pharmacy is transmitted over a third network connection by the server patient portal application to a client patient portal application executing on a patient computing device operated by the patient, wherein a selection of the identity of the pharmacy is received by the client patient portal application from the patient, wherein the identity of the pharmacy is transmitted over the third network connection by the client patient portal application to the server patient portal application;

subsequent to discarding the precursor data from the computer-readable storage of the server EHR, receiving the precursor data and the identity of the pharmacy from the server patient portal application over the second network connection;

subsequent to receiving the precursor data and the identity of the pharmacy from the server patient portal application, constructing the electronic prescription using the precursor data, the identity of the pharmacy, and an electronic signature for the healthcare worker; and causing the electronic prescription to be transmitted over a fourth network connection to a computing system operated by the pharmacy.

16. The non-transitory computer-readable storage medium of claim 15, the acts further comprising:

responsive to constructing the electronic prescription, transmitting the electronic prescription over the fourth network connection to a hub application executing on a hub computing system, wherein the electronic prescription is routed by the hub application to the computing system operated by the pharmacy based on the identity of the pharmacy in the electronic prescription.

17. The non-transitory computer-readable storage medium of claim 15, wherein the precursor data further includes:

an identity of the healthcare worker;

a dosage amount of the controlled substance for the patient; and an indication as to how often the patient is to consume the controlled substance.

18. The non-transitory computer-readable storage medium of 15, wherein the electronic prescription further comprises a date on which constructing the electronic prescription occurred.

19. The non-transitory computer-readable storage medium of claim 15, wherein constructing the electronic prescription comprises:

transmitting, over the first network connection, a notification to the client EHR indicating that the patient has selected the pharmacy to provide the controlled substance, the notification comprising the precursor data and the identity of the pharmacy, wherein authorization credentials for the healthcare worker are received by the client EHR, and further wherein the authorization credentials are transmitted by the client EHR over the first network connection to the server EHR; and subsequent to receiving the authorization credentials for the healthcare worker from the client EHR, constructing the electronic prescription.

20. The non-transitory computer-readable storage medium of claim 15, wherein the patient computing device is a mobile computing device.

* * * * *